US008170678B2

(12) United States Patent
Polak

(10) Patent No.: US 8,170,678 B2
(45) Date of Patent: May 1, 2012

(54) SYNCHRONIZED DIAGNOSTIC MEASUREMENT FOR COCHLEAR IMPLANTS

(75) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 462 days.

(21) Appl. No.: 12/417,041

(22) Filed: Apr. 2, 2009

(65) Prior Publication Data

US 2009/0254149 A1 Oct. 8, 2009

Related U.S. Application Data

(60) Provisional application No. 61/042,054, filed on Apr. 3, 2008.

(51) Int. Cl.
*A61N 1/00* (2006.01)

(52) U.S. Cl. ........................................................ 607/57

(58) Field of Classification Search ................ 607/55–63
See application file for complete search history.

(56) References Cited

U.S. PATENT DOCUMENTS

| 5,626,629 | A | 5/1997 | Faltys et al. ..................... 607/57 |
| 5,938,691 | A | 8/1999 | Schulman et al. ............... 607/57 |
| 6,195,585 | B1 | 2/2001 | Karunasiri et al. .............. 607/57 |
| 2006/0247735 | A1 | 11/2006 | Honert ............................. 607/57 |
| 2006/0276856 | A1 | 12/2006 | Soli et al. ........................ 607/57 |
| 2006/0287690 | A1 | 12/2006 | Bouchataoui et al. .......... 607/57 |
| 2007/0244410 | A1 | 10/2007 | Fridman et al. ................. 600/554 |
| 2009/0259140 | A1 | 10/2009 | Buchman et al. ............... 600/559 |

OTHER PUBLICATIONS

Brown, Carolyn J., et al "Electrically Evoked Whole Nerve Action Potential in Ineraid Cochlear Implant Users: Responses to Different Stimulating Electrode Configurations and Comparison to Psychophysical Responses", *Journal of Speech and Hearing Research*, vol. 39, Jun. 1996, pp. 453-467.
Gantz, Bruce J., et al "Intraoperative Measures of Electrically Evoked Auditory Nerve Compound Action Potential", *The American Journal of Otology*, vol. 15, No. 2, Mar. 1994, pp. 137-144.
Guedes, Mariana C., et al "Neural Response Telemetry Measures in Patients Implanted with Nucleus 24®", *Revista Brasileira de Otorrinolaringologia*, vol. 71, No. 5, Sep. 2005, pp. 660-667, XP002515865, ISSN: 0034-7299, sections "Material and method", "Results", "Discussion".
Klop, W. Martin C., et al "A New Method for Dealing with the Stimulus Artefact in Electrically Evoked Compount Action Potential Measurements", *Acta Oto-Laryngologica*, Scandinavian Univ. Press, Oslo, NO. vol. 124, No. 2, Mar. 1, 2004, pp. 137-143, XP009112350, ISSN: 0001-6489, abstract sections "Introduction", "Results—Artefact".
Ragheb, T., et al "The Polarization Impedance of Common Electrode Metals Operated at Low Current Density", *Annals of Biomedical Engineering* Pergamon Press, Oxford, GB, vol. 19, No. 2, Jan. 1, 1991, pp. 151-163, XP009112328, ISSN: 0090-6964 cited in the application the whole document.
International Searching Authority International Search Report and Written Opinion, PCT/US2008/083371, Feb. 19, 2009.
International Searching Authority International Search Report and Written Opinion, PCT/US2009/039245, May 18, 2009.
International Bureau of WIPO PCT Notification Concerning Availability of the Publication of the International Application, PCT/US2009/067073, Jul. 8, 2010.

*Primary Examiner* — Scott Getzow
(74) *Attorney, Agent, or Firm* — Sunstein Kann Murphy & Timbers LLP

(57) ABSTRACT

Objective measurement of cochlear implant operation is described which coordinates the delivery to a patient of an acoustic signal and an electrical signal. The acoustic signal is developed as an acoustic stimulation input to the ear canal of a patient, and the electrical signal is developed as an electrical stimulation input to intracochlear electrodes of a cochlear implant. The evoked response in the patient to the delivered signals is then measured.

10 Claims, 4 Drawing Sheets

SYNCHRONIZED DIAGNOSTIC MEASUREMENT FOR COCHLEAR IMPLANTS

This application claims priority from U.S. Provisional Patent Application 61/042,054, filed Apr. 3, 2008, which is incorporated herein by reference.

FIELD OF THE INVENTION

The present invention relates to medical implants, and more specifically to diagnostic measurement in cochlear implant systems.

BACKGROUND ART

Cochlear implants (CI) help profoundly deaf or severely hearing impaired persons to perceive environmental sounds. Unlike conventional hearing aids which just apply an amplified and modified sound signal, a cochlear implant is based on direct electrical stimulation of the auditory nerve so that hearing impressions most similar to normal hearing are obtained.

A cochlear implant system consists of two main parts, an external speech processor and the implanted stimulator. The speech processor contains a power supply and is used to perform signal processing of an acoustic input signal to extract stimulation parameters for the implanted stimulator. The implanted stimulator generates stimulation patterns and delivers them to auditory nervous tissue by an electrode array which usually is positioned in the scala tympani in the cochlea. A wireless connection between the speech processor and the implanted stimulator can be established by encoding digital information in an rf-channel and coupling the signal percutaneously using an inductive coupled coils arrangement. The implanted stimulator decodes the information by envelope detection of the rf signal.

Stimulation strategies employing high-rate pulsatile stimuli in multi-channel electrode arrays have proven to be successful in giving high levels of speech recognition. One example is the Continuous Interleaved Sampling (CIS) strategy, as described by Wilson et al., *Better Speech Recognition With Cochlear Implants*, Nature, vol. 352:236-238 (1991), which is incorporated herein by reference. For CIS, symmetrical biphasic current pulses are used which are strictly non-overlapping in time. The rate per channel typically is higher than 800 pulses/sec. Other stimulation strategies may be based on simultaneous activation of electrode currents.

For high-rate pulsatile stimulation strategies, some patient specific parameters typically need to be determined. This is done some weeks after surgery in a fitting procedure. For given phase duration of stimulation pulses and for a given stimulation rate, two key parameters to be determined for each stimulation channel include:

1. the minimum amplitude of biphasic current pulses necessary to elicit a hearing sensation (Threshold Level, or THL); and 2. the amplitude resulting in a hearing sensation at a comfortable level (Most Comfortable Level, or MCL).

For stimulation, only amplitudes between MCL and THL for each channel are used. The dynamic range between MCL and THL typically is between 6-12 dB. However, the absolute positions of MCLs and THLs vary considerably between patients, and differences can reach up to 40 dB. To cover these absolute variations, the overall dynamic range for stimulation in currently used implants is typically about 60 dB.

There are several methods of setting the MCLs and THLs. For example, they can be estimated during the fitting procedure by applying stimulation pulses and asking the patient about his/her subjective impression. This method usually works without problems with postlingually deaf patients. However, problems occur with prelingually or congenitally deaf patients, and in this group, all ages—from small children to adults—are concerned. These patients are usually neither able to interpret nor to describe hearing impressions, and only rough estimations of MCLs and THLs are possible based on behavioral methods. Especially the situation of congenitally deaf small children needs to be mentioned here. An adequate acoustic input is especially important for the infant's speech and hearing development, and this input in many cases can be provided with a properly fitted cochlear implant.

One approach for an objective measurement of MCLs and THLs is based on the measurement of the EAPs (Electrically Evoked Action Potentials), as described by Gantz et al., *Intraoperative Measures of Electrically Evoked Auditory Nerve Compound Action Potentials,* American Journal of Otology 15 (2):137-144 (1994), which is incorporated herein by reference. In this approach, the recording electrode is usually placed at the scala timpani of the inner ear. The overall response of the auditory nerve to an electrical stimulus is measured very close to the position of the nerve excitation. This neural response is caused by the super-position of single neural responses at the outside of the axon membranes. The amplitude of the EAP at the measurement position is between 10 $\mu$V and 1800 $\mu$V. Information about MCL and THL at a particular electrode position can first of all be expected from the so called "amplitude growth function," as described by Brown et al., *Electrically Evoked Whole Nerve Action Potentials In Ineraid Cochlear Implant Users: Responses To Different Stimulating Electrode Configurations And Comparison To Psychophysical Responses,* Journal of Speech and Hearing Research, vol. 39:453-467 (June 1996), which is incorporated herein by reference. This function is the relation between the amplitude of the stimulation pulse and the peak-to-peak voltage of the EAP. Another interesting relation is the so called "recovery function" in which stimulation is achieved with two pulses with varying interpulse intervals. The recovery function as the relation of the amplitude of the second EAP and the interpulse interval allows conclusions to be drawn about the refractory properties and particular properties concerning the time resolution of the auditory nerve.

Besides cochlear implant systems as such, some subjects with some residual hearing (partial deafness) are now benefiting from hybrid systems such as combined electric and acoustic stimulation (EAS) as was first described in von Ilberg et al., *Electric-Acoustic Stimulation Of The Auditory System,* ORL 61:334-340 (1999), which is incorporated herein by reference. EAS systems combine the use of a conventional hearing aid (HA) device to provide acoustic-mechanical stimulation of lower audio frequencies to the subject's ear drum and a cochlear implant (CI) to provide intracochlear electrical stimulation of higher audio frequencies to the auditory nerve. For example, see Lorens et al., *Outcomes Of Treatment Of Partial Deafness With Cochlear Implantation: A DUET Study,* Laryngoscope, Feb. 2008: 118 (2):288-94, which is incorporated herein by reference.

SUMMARY OF THE INVENTION

Embodiments of the present invention are directed to objective diagnostic measurement for cochlear implant patients utilizing synchronized acoustic and electrical signals. The acoustic signal is developed as an acoustic stimulation input in the ear canal of a patient, and the electrical signal is developed as an electrical stimulation input to intracochlear electrodes in a cochlear implant. The evoked response in the patient to the delivered signals is then measured.

In further specific embodiments, the measured response may be analyzed to diagnose auditory perception of the patient. For example, this may include determining a frequency-specific response relative to specific position of the electrodes in the cochlea. An embodiment may be used to customize operation of the cochlear implant for the patient based on the measured response.

In a specific embodiment, measuring the evoked response may include measuring a near field response in associated tissue near to the intracochlear electrodes and/or measuring a far field response associated with the skin surface of the patient.

Coordinating the delivery of the stimulation inputs may include coordinating a delay time between the acoustic signal and the electrical signal. In some embodiments, the cochlear implant may be a bilateral cochlear implant.

DETAILED DESCRIPTION OF SPECIFIC EMBODIMENTS

Embodiments of the present invention are directed to an objective measurement system for a cochlear implant which coordinates and synchronizes an acoustic stimulus and an electrical stimulus of remaining hair cells and neural cells. The resulting evoked response is recorded and analyzed with near and/or far field measurements. This arrangement is especially useful in diagnostics of patients implanted with a cochlear implant (e.g., partial deafness), helping to optimize the fit for patients of their speech processor and the cochlear implant stimulation. These measurements can also be useful for identifying properties of the auditory nerve and higher levels of the auditory pathway and for acquiring information regarding the preservation of the remaining hearing in a patient. The combination of the near field and far field recordings may specifically be useful for identifying frequency specific placement of the stimulation electrodes within the cochlea. A system may also be useful for research purposes such as into the properties of frequency and/or time dependent stimuli, information about the movement of the basilar membrane, obtaining important indications as to whether electrical stimulation directly stimulates the remaining hair cells or whether it stimulates cells of the auditory nerve or for developing of new speech coding strategies for cochlear implants.

Figure 1:
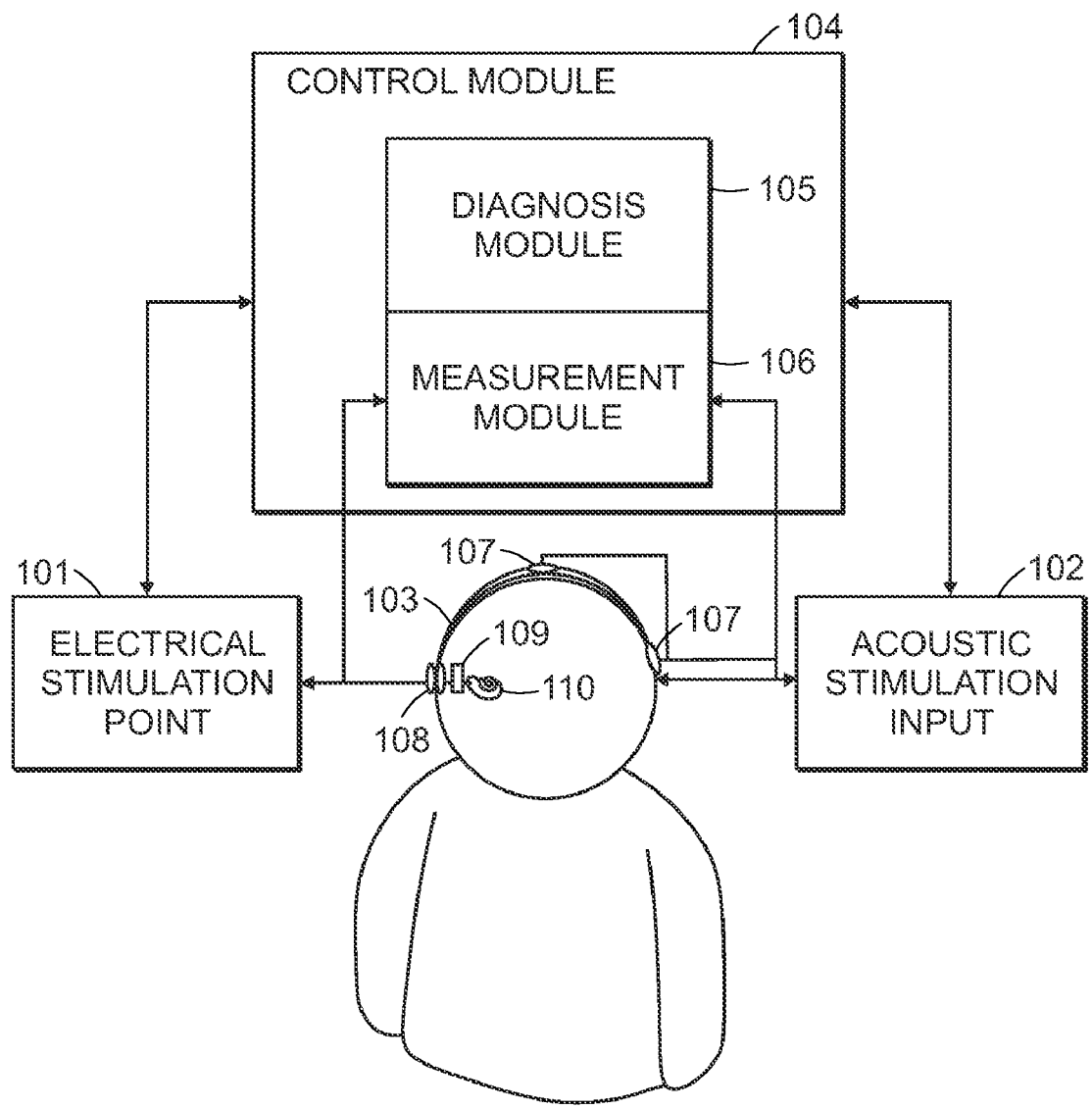
FIG. 1 shows various functional blocks in one specific embodiment of the present invention.

FIG. 1 shows one example of a specific objective measurement system in which an acoustic stimulation input 102 develops an acoustic signal in the ear canal of a patient 103. An electrical stimulation input 101 also develops an electrical signal for intracochlear electrodes 110 in a cochlear implant 109 in the patient 103. Typically, a percutaneous inductive coil arrangement 108 would be used to couple the electrical signal from the electrical stimulation input 101 across the skin of the patient 103 into the cochlear implant 109. FIG. 1 shows a unilateral cochlear implant 109 on just one side of the patient 103, but other embodiments may be based on a bilateral system of cochlear implants on both the left and right sides of the patient 103. A control module 104 coordinates the delivery of the acoustic signal and the electrical signal by the acoustic stimulation input 102 and electrical stimulation input 101 respectively. For example, the control module 104 may coordinate the signal delivery by coordinating a delay time between the acoustic signal and the electrical signal. A measurement module 106 measures the evoked response in the patient 103 to the delivered signals. In specific embodiments, these elements may be implemented as dedicated hardware devices, or computer software running on generic or specific computer devices, or some combination of hardware and software.

In the specific embodiment shown in FIG. 1, the measurement module 106 is within and a part of the control module 104. For example, the measurement module 106 may be a software routine which forms a part of a larger software application that constitutes the control module 104. In other embodiments, the measurement module 106 and the control module 104 may be separate and independent, and indeed, may run on different computers. Similarly, in some embodiments, the electrical stimulation input 101 and/or the acoustic stimulation input 102 may be developed by or delivered by their own associated computers which may or may not be separate and independent of the control module 104 and any other associated computer.

The system shown in FIG. 1 also includes a diagnosis module 105 for analyzing the measured response to diagnose the auditory perception of the patient. For example, the diagnosis module 105 may analyze the measured response by determining a frequency-specific response relative to the specific position of the electrodes in the cochlea. An embodiment may also include a fitting module for customizing operation of the cochlear implant for the patient 103 based on the response developed by the measurement module 106. Such a fitting module may be a separate device or software module, or may form a portion of one of the other system elements such as the measurement module 106 or the diagnosis module 105.

To develop the evoked response measurement, the cochlear implant 109 and the intracochlear electrodes 110 may include one or more near field measurement sensors for measuring a near field response in associated tissue near to the intracochlear electrodes 110. Also shown are one or more far field measurement sensors 107 for measuring a far field response associated with the skin surface of the patient.

Using the coordinated and synchronized electrical stimulation input 101 and acoustic stimulation input 102 several types of evoked potentials can be recorded. Near field recordings (i.e. from the implanted intracochlear electrodes 110) and/or far field recordings, e.g., from the far field sensing electrodes 107 placed on the head according to the specific types of the auditory evoked potentials measurements. Possible measurements may include short latency responses such as compound action potentials and auditory brainstem responses, middle late potentials such as middle late responses, and late cortical responses resulting from the electric and acoustic stimulation.

Figure 2:
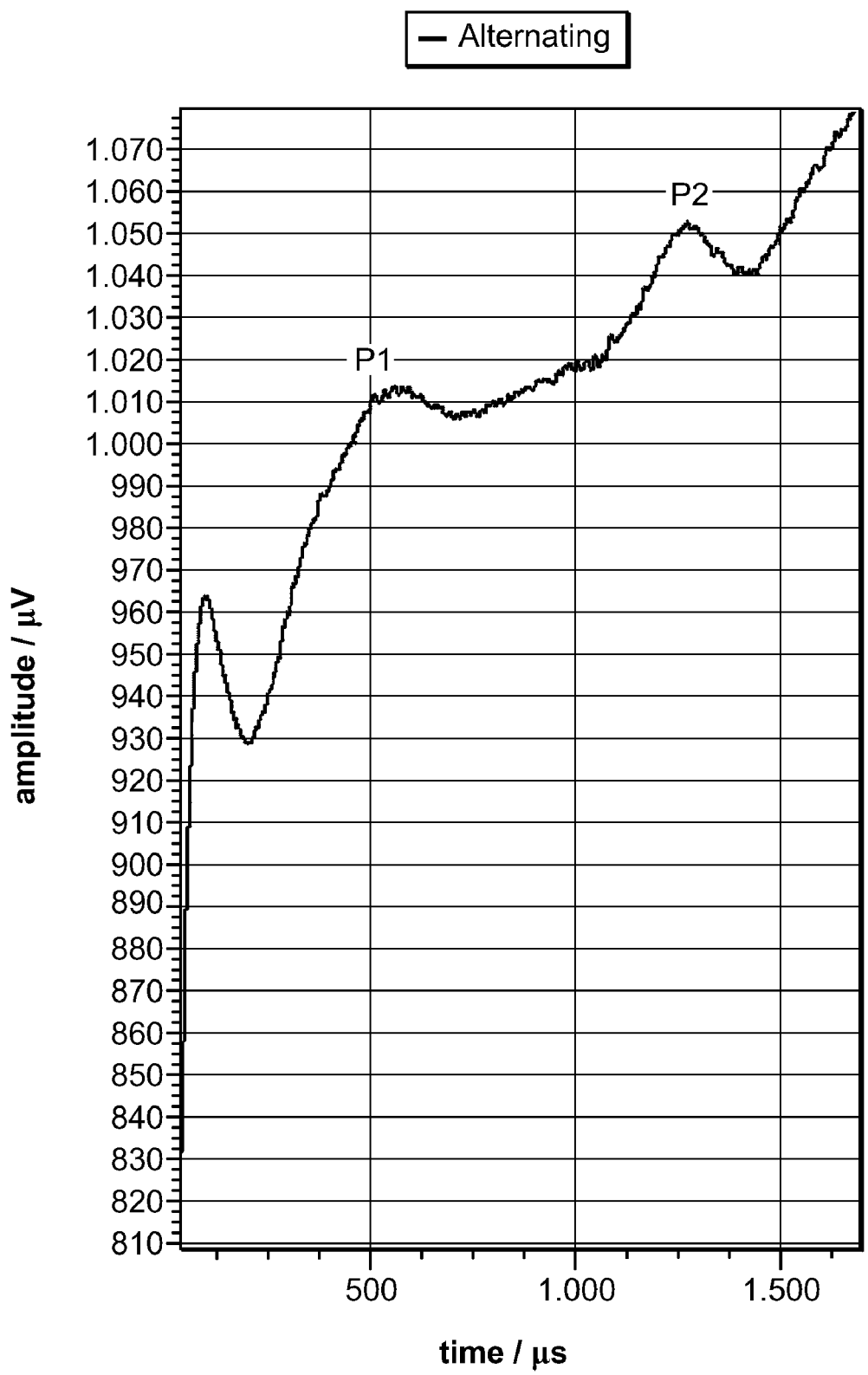
FIG. 2 shows an example of the measured evoked response representing a near field recording from the synchronized electrical and acoustic stimulation inputs.
Figure 3:
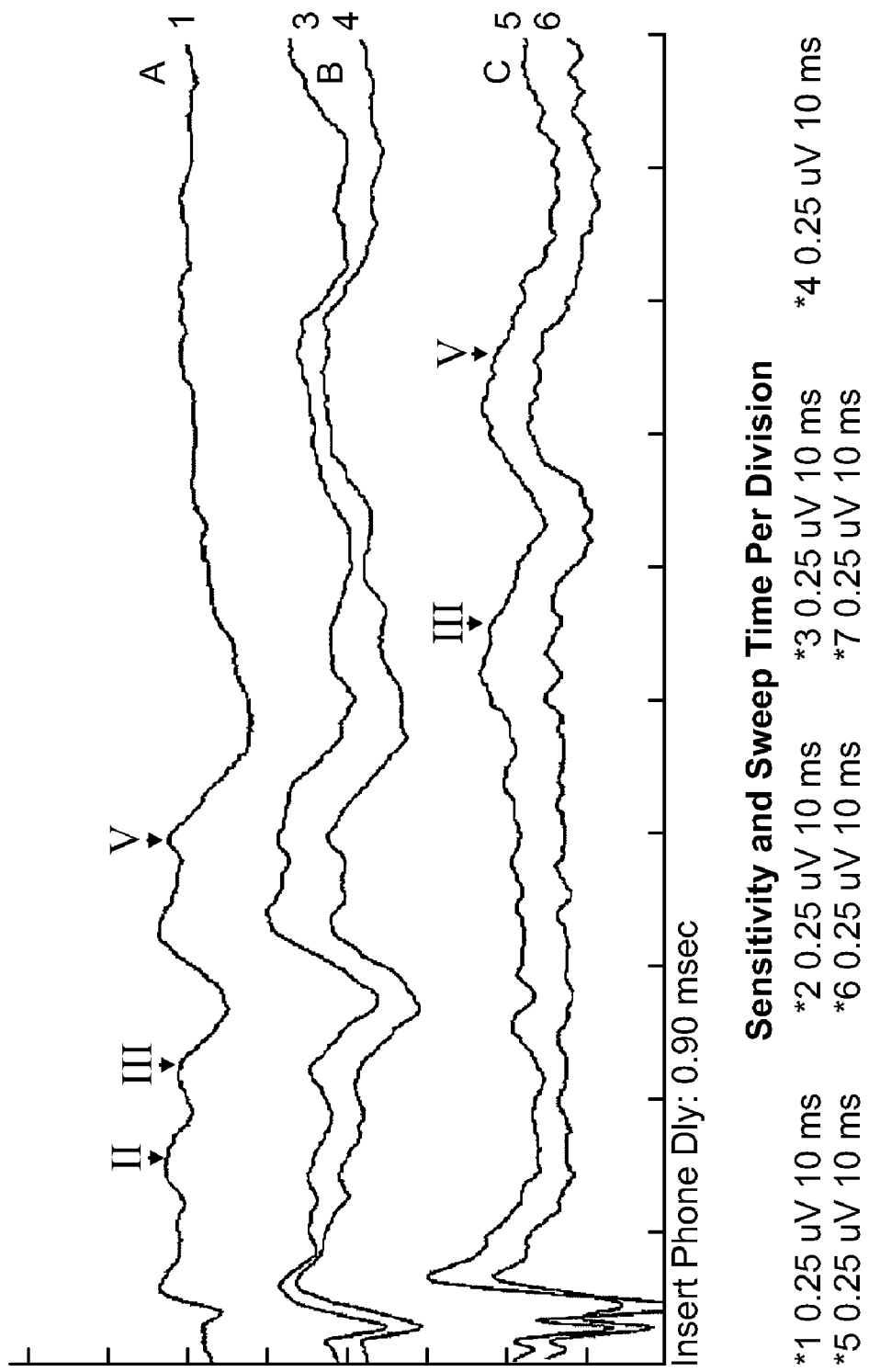
FIG. 3 shows an example of the measured evoked response representing a far field recording from the synchronized electrical and acoustic stimulation inputs in a first patient.
Figure 4:
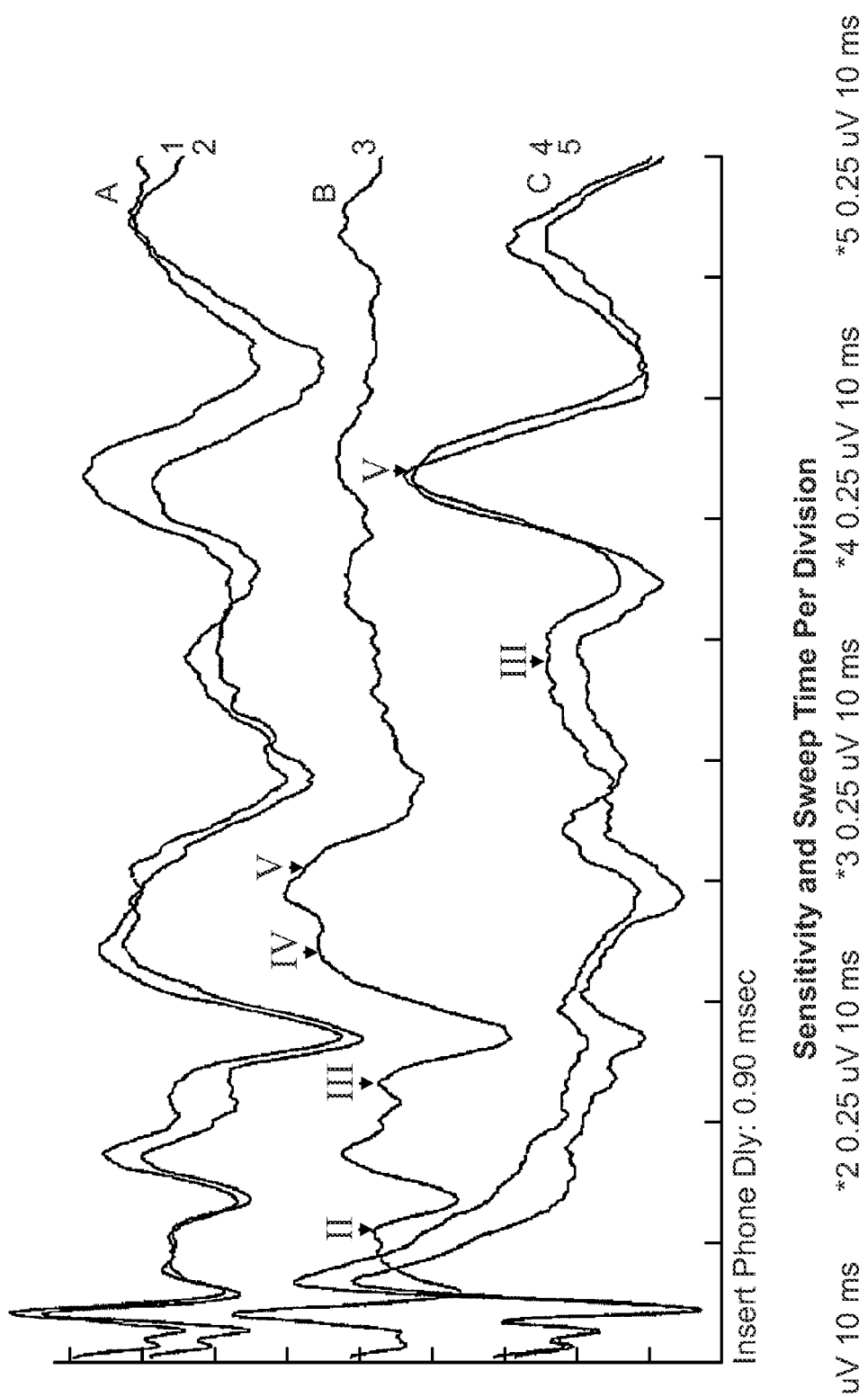
FIG. 4 shows an example of the measured evoked response representing a far field recording from the synchronized electrical and acoustic stimulation inputs in a second patient.

FIG. 2 shows an example of the measured evoked response of a near field recording resulting from the synchronized electrical and acoustic stimulation inputs. Specifically, FIG. 2 shows measurement of acoustically and electrically evoked compound action potential near the intracochlear electrodes 110 from the synchronized electrical stimulation input 101 and acoustic stimulation input 102 at the most comfortable level for the patient 103. FIG. 3 shows an example of far field recordings from a first patient at the most comfortable level of acoustic and electrical stimuli. Trace A shows a set of far field recordings for electrical stimulation only, Trace B shows an example with both acoustic and electrical stimulation, and Trace C shows acoustic stimulation only. FIG. 4 shows a similar set of traces for a second patient where Trace A shows recordings obtained from electrical and acoustic stimulation at the most comfortable level, Trace B shows electrical stimulation at the most comfortable level and acoustic stimulation at 10 dB lover level than the patient's most comfortable level, and Trace C shows acoustic stimulation at the most comfortable level.

Embodiments of the present invention may be especially useful for EAS patients because of their better preserved hearing postoperatively. For example, EAS patients as a group demonstrate significantly higher post-operative speech score results than regular CI patients. In EAS patients, the optimal cochlear implant (CI) parameters as determined from the measurements obtained by embodiments of the present invention may in turn influence hearing aid (HA) parameters, e.g., the frequency ranges of each. And rather than just an implanted speech processor for the CI, EAS systems may also be based on an overall system speech processor which coordinates the operation of both the cochlear implant (CI) and the acoustic-mechanical hearing aid (HA).

Embodiments of the invention may be implemented in any conventional computer programming language. For example, preferred embodiments may be implemented in a procedural programming language (e.g. "C") or an object oriented programming language (e.g., "C++", Python). Alternative embodiments of the invention may be implemented as preprogrammed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for objective diagnostic measurement for cochlear implant subjects, the method comprising:
    in an audio diagnostic measurement system:
        coordinating the delivery to a patient of an acoustic signal and an electrical signal so that:
            i. the acoustic signal is developed as an acoustic stimulation input to the ear canal of a patient, and
            ii. the electrical signal is developed as an electrical stimulation input to intracochlear electrodes of a cochlear implant; and
            iii. wherein coordinating the delivery includes coordinating a delay time between the acoustic signal and the electrical signal;
        measuring the evoked response in the patient to the delivered signals including:
            i. measuring a near field response associated tissue near the intracochlear electrodes, and
            measuring a far field response associated with the skin surface of the patient.

2. A method according to claim 1, further comprising:
    analyzing the measured response to diagnose auditory perception of the patient.

3. A method according to claim 2, wherein diagnosing the auditory perception includes determining a frequency-specific response relative to specific position of the electrodes in the cochlea.

4. A method according to claim 1, further comprising:
    customizing operation of the cochlear implant for the patient based on the measured response.

5. A method according to claim 1, wherein the cochlear implant is a bilateral cochlear implant.

6. An objective measurement system for a cochlear implant, the system comprising:
    an acoustic stimulation input for developing an acoustic signal to the ear canal of a patient;
    an electrical stimulation input for developing an electrical signal for intracochlear electrodes of a cochlear implant;
    a control module for coordinating the delivery of the acoustic signal and the stimulation signal by coordinating a delay time between the acoustic signal and the electrical signal; and
    a measurement module for measuring the evoked response in the patient to the delivered signals, including:

i. at least one near field measurement sensor for measuring a near field response in associated tissue near the intracochlear electrodes, and ii. at least one far field measurement sensor for measuring a far field response associated with the skin surface of the patient.

7. A system according to claim 6, further comprising:

a diagnosis module for analyzing the measured response to diagnose auditory perception of the patient.

8. A system according to claim 7, wherein the diagnosis module analyzes the measured response by determining a frequency-specific response relative to specific position of the electrodes in the cochlea.

9. A system according to claim 6, further comprising:

a fitting module for customizing operation of the cochlear implant for the patient based on the measured response.

10. A system according to claim 6, wherein the cochlear implant is a bilateral cochlear implant.

* * * * *